(12) United States Patent
Keikhaee et al.

(10) Patent No.: US 10,392,147 B2
(45) Date of Patent: Aug. 27, 2019

(54) STERILIZATION UNIT FOR A FILLING MACHINE

(71) Applicant: TETRA LAVAL HOLDINGS & FINANCE S.A., Pully (CH)

(72) Inventors: Manoochehr Keikhaee, Bunkeflostrand (SE); Rasmus Nystrom, Malmo (SE); Jorgen Riis Mork, Vipperod (DK)

(73) Assignee: TETRA LAVAL HOLDINGS & FINANCE S.A., Pully (CH)

(*) Notice: Subject to any disclaimer, the term of this patent is extended or adjusted under 35 U.S.C. 154(b) by 293 days.

(21) Appl. No.: 15/338,042

(22) Filed: Oct. 28, 2016

(65) Prior Publication Data
US 2017/0043894 A1    Feb. 16, 2017

Related U.S. Application Data

(62) Division of application No. 14/372,630, filed as application No. PCT/EP2013/050360 on Jan. 10, 2013, now Pat. No. 9,481,483.

(30) Foreign Application Priority Data

Jan. 16, 2012  (SE) ....................... 1250020

(51) Int. Cl.
   A61L 2/10    (2006.01)
   A61L 2/18    (2006.01)
   (Continued)

(52) U.S. Cl.
   CPC .............. B65B 55/08 (2013.01); A61L 2/06 (2013.01); A61L 2/10 (2013.01); A61L 2/186 (2013.01); B65B 55/10 (2013.01)

(58) Field of Classification Search
   CPC .................... B65B 55/10; B65B 39/02
   (Continued)

(56) References Cited

U.S. PATENT DOCUMENTS 4,201,251 A * 5/1980 Bennett ................. B65B 57/06
                                                        141/155
5,350,568 A   9/1994 Tuckner et al.
(Continued)

FOREIGN PATENT DOCUMENTS

EP    0 394 734 A1    10/1990
EP    0 597 355 A2    5/1994
(Continued)

OTHER PUBLICATIONS

Office Action (Notice of Reasons for Rejection) dated Oct. 17, 2016 by the Japanese Patent Office in corresponding Japanese Patent Application No. 2014-551606, and an English Translation of the Office Action. (7 pages).

(Continued)

*Primary Examiner* — Kevin Joyner
*Assistant Examiner* — Holly M Mull
(74) *Attorney, Agent, or Firm* — Buchanan Ingersoll & Rooney PC

(57) ABSTRACT

A sterilization unit comprises at least one nozzle pipe for injection of a sterilization agent into a packaging container to be sterilized. The sterilization unit is driven to move in an axial direction, in a downward stroke and an upward stroke, corresponding to a longitudinal direction of the nozzle pipe such that it is inserted into an open end of the packaging container during sterilization thereof. The nozzle pipe is suspended such as to be displaceable in relation to the sterilization unit, in the axial direction.

21 Claims, 2 Drawing Sheets

(51) Int. Cl.
  *B65B 55/08* (2006.01)
  *B65B 55/10* (2006.01)
  *A61L 2/06* (2006.01)

(58) Field of Classification Search
  USPC .......................................................... 422/24
  See application file for complete search history.

(56) References Cited

U.S. PATENT DOCUMENTS

| | | | | |
|---|---|---|---|---|
| 5,944,709 | A * | 8/1999 | Barney | ............... A61J 1/10 |
| | | | | 206/219 |
| 6,338,235 | B1 | 1/2002 | Bentz et al. | |
| 6,692,684 | B1 | 2/2004 | Nantin et al. | |
| 2004/0089369 | A1 | 5/2004 | Armbruster et al. | |
| 2004/0208781 | A1 | 10/2004 | Hayashi et al. | |
| 2006/0159583 | A1 * | 7/2006 | Naslund | ............... B65B 55/027 |
| | | | | 422/22 |
| 2009/0148340 | A1 * | 6/2009 | Hansen | ............... A61L 2/0011 |
| | | | | 422/22 |
| 2010/0199605 | A1 | 8/2010 | Boldrini | |
| 2011/0072759 | A1 | 3/2011 | Mielnik et al. | |
| 2012/0279177 | A1 * | 11/2012 | Macquet | ............... B65B 7/2835 |
| | | | | 53/426 |

FOREIGN PATENT DOCUMENTS

| | | |
|---|---|---|
| EP | 1 046 585 A3 | 5/2002 |
| EP | 1 220 787 B1 | 9/2003 |
| JP | H07-002203 A | 1/1995 |
| JP | H10-119935 A | 5/1998 |
| JP | 2004-059014 A | 2/2004 |
| WO | WO 01/28863 A1 | 4/2001 |
| WO | WO 2009/016500 A1 | 2/2009 |

OTHER PUBLICATIONS

International Search Report (PCT/ISA/210) dated Jul. 30, 2013, by the European Patent Office as the International Searching Authority for International Application No. PCT/EP2013/050360.

Written Opinion (PCT/ISA/237) dated Jul. 30, 2013, by the European Patent Office as the International Searching Authority for International Application No. PCT/EP2013/050360.

* cited by examiner

STERILIZATION UNIT FOR A FILLING MACHINE

CROSS REFERENCE TO RELATED APPLICATIONS

This application is a divisional application of U.S. patent application Ser. No. 14/372,630 filed on Jul. 16, 2014, which is a U.S. National Stage application of International Patent Application No. PCT/EP2013/050360 filed on Jan. 10, 2013, which claims priority to Swedish Patent Application No. 1250020-3 filed on Jan. 16, 2012, the entire contents of all three of which are incorporated herein by reference.

FIELD OF THE INVENTION

The present invention relates to an arrangement in a filling machine utilized for filling of liquid foodstuff into packaging containers. In particular it relates to an arrangement in a sterilization section of such filling machine.

BACKGROUND

Before filling packaging containers with liquid foodstuff it is common to perform a sterilization procedure, in which a liquid or vaporized sterilization agent is injected into the interior of the packaging container in order to eliminate any microorganisms present.

Within the field of the present applicant the packaging container is formed from a laminated material comprising layers of paper and thermoplastic material. The choice of thermoplastic material as well as the presence of any further layers, such as aluminium foil or other metal foil, or additional barrier layers, will depend on the type of product to be contained and the desired shelf-life for such product. A minimum criterion is that the interior of the packaging container should not absorb moisture to the extent that the integrity of the packaging container is jeopardized. In most cases the same is true for the outside. Further barrier layers, of which aluminium foil is one example, may be arranged to prevent light or oxygen from diffusing into the packaging container after it has been sealed. Such measures may be desired in instances where an extended shelf-life is desired. While these measures relate to what can be done in order to maintain the conditions after a packaging container is filled and sealed, the present invention is closer related to the measures performed in order to obtain proper conditions prior to filling of the container.

An example is disclosed in the publication EP-1 046 585 by the present applicant, which should be sufficient in order for the skilled person to grasp the background and aid in realization of the beneficial features of the present invention.

SUMMARY

The present invention concerns a sterilization unit for a filling machine. The sterilization unit comprises at least one nozzle pipe for injection of a sterilization agent into a packaging container to be sterilized, and the sterilization unit is driven to move in an axial direction, in a downward stroke and an upward stroke, corresponding to a longitudinal direction of the nozzle pipe such that it is inserted into an open end of the packaging container during sterilization thereof. The sterilization device is characterized in that the nozzle pipe is suspended such as to be displaceable in relation to the sterilization unit, in the axial direction.

The advantage of having a displaceable suspension will be evident from the detailed description. It should be emphasized that "downward stroke" and "upward stroke" refers to the expected direction in a filling machine where a package is sterilized from an open end directed upwards, through which it is subsequently filled with contents. This also corresponds to the direction in the embodiment shown in the detailed description. In that respect "downward" and "upward" could be replaced by "outward" and "inward", "forward" and "backward" or another pair of opposing directions in case the packages does not have a vertical orientation and are being sterilized from above.

To further increase the killing efficiency the sterilization unit may comprise a plate provided with holes allowing passage of the nozzle pipe during sterilization. The plate should preferably cover the extension of the open end of the packaging containers, and it may also be advantageous if a single plate covers all packaging containers currently processed in the sterilization unit. The plate will maintain the sterilization agent in the interior of the packaging container to a higher extent, and sterilization agent leaving the interior of the packaging container will also to a higher extent be directed downwards where it may have a sterilization effect on the outside of the packaging container, and at least on an upper region thereof. In an embodiment where the plate is static it will be arranged such that there is a clearance between a lower edge of the plate and the uppermost end of the packages, to allow passage of the packages. In an embodiment where the plate is moveable to some extent together with the sterilization unit such clearance may be even smaller or non-existing after the packages have been indexed to the correct position.

In one or more embodiments the nozzle pipe may have a length exceeding the length of a single stroke of the sterilization unit. This will be further described in the detailed description of the present application. It is preferred that the nozzle pipe is rectilinear along this length.

In one or several embodiments the nozzle pipe has a constant cross section over at least a length corresponding to the length of a single stroke of the sterilization unit, such that it may move freely when needed.

In another embodiment the suspension of the nozzle pipe is provided by a sleeve with a through hole in the axial direction, the sleeve being rigidly attached to the sterilization unit. The use of a sleeve is one of the simpler, and still preferred, embodiments of the present invention. The sleeve may or may not apply a clamping force onto the nozzle pipe, and if such a clamping force is to be applied it may be effected by the sleeve being resilient or by the intermediate of some resilient means, such as a spring or an o-ring between the sleeve and the nozzle pipe.

In a related embodiment the nozzle pipe is provided with a section of extended diameter remote to its free end. The section of extended diameter will enable the sleeve to locate the nozzle pipe in one of the axial directions, i.e. prevent it from falling downwards into the packaging container, in a very simple manner. The section of extended diameter may be provided by a coupling which fluidly connects the nozzle pipe with a flexible line through which the sterilization agent is delivered, meaning that the number of components used is kept low.

DETAILED DESCRIPTION OF EMBODIMENTS

Figure 1:
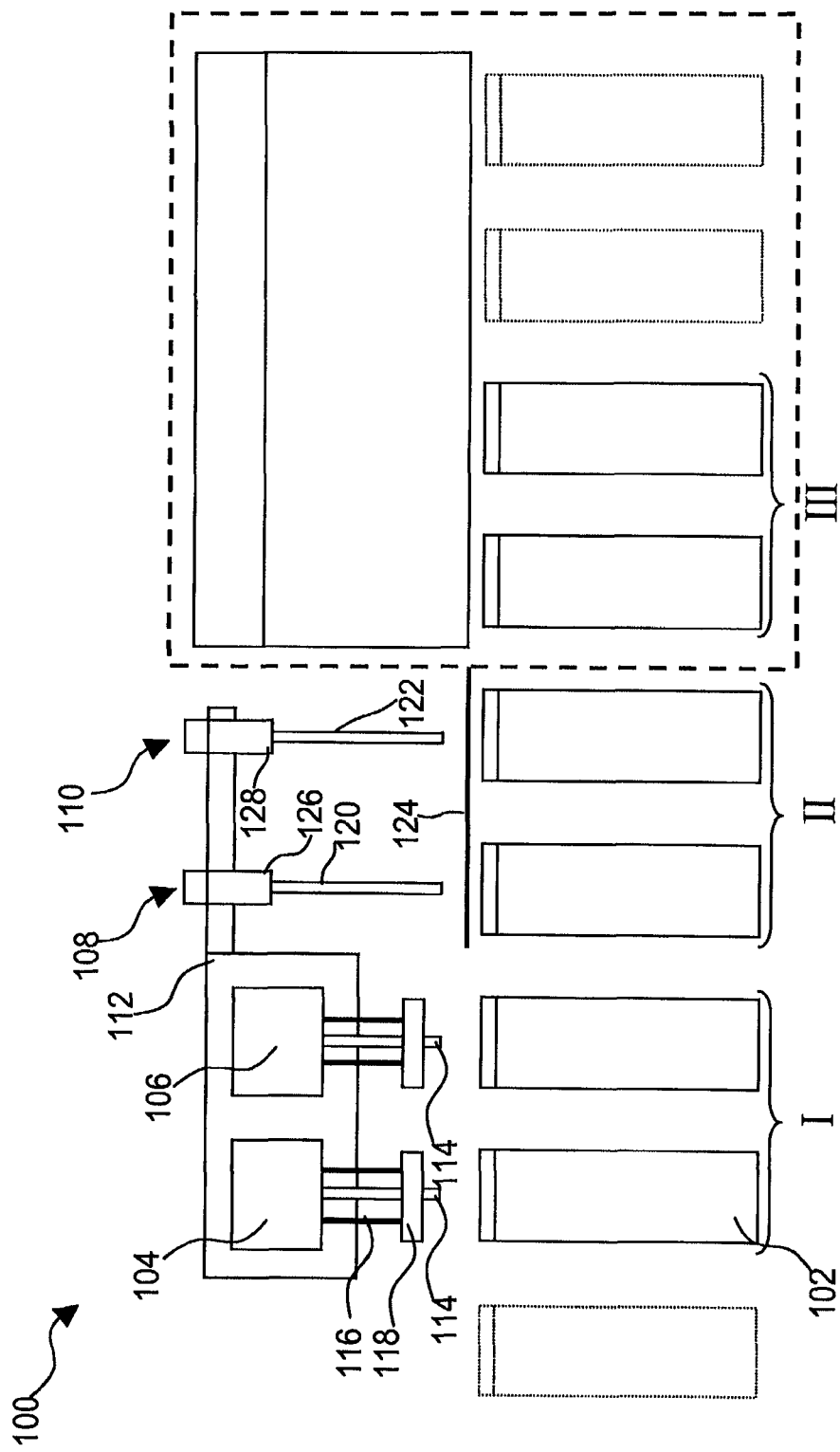
FIG. 1 is a schematical side view of the sterilization section of a filling machine, including an embodiment of the present invention in a first operational state.

The present invention will now be described by virtue of an embodiment thereof. FIG. 1 illustrates a segment of a filling machine, and in particular a sterilization section thereof. It should be emphasized that the drawing is schematic only, individual components does not necessarily have the illustrated design, since the detailed design is not relevant for the functional description of the invention, which still will be detailed enough for the skilled person to be able to work the invention. In the present context "sterilization" and similar terms should be construed as providing a sterilization agent to a packaging container, rather than a quantitative measure of the actual effect of the act.

Starting with the general flow, packaging containers 102 follow a machine direction from left to right (referring to FIG. 1). They are indexed two positions between processing activities, which is illustrated by the brackets provided with roman numerals (I, II, and III). Prior to entering the illustrated section of the filling machine the containers 102 have been formed and provided with a closed end, now facing downwards. The closed end may be accomplished by sealing and folding one end of a tubular sleeve of packaging material, yet it may also be accomplished by providing one end of the tubular sleeve of material with a top of an alternative material, such as plastic, which was described in the summary. In the is context "sleeve" should include a tubular shape with any cross section, such as rectangular, oval, prismatic etc, wherein the cross section may vary along the extension of the tubular shape. The invention as such is found in processing step II, though embodiments of the invention may also incorporate procedures and elements from neighbouring processing steps.

The material of the sleeve includes a laminated material comprising layers of paper and thermoplastic material. In the preferred embodiment aluminium foil or other metal foil is added as a further barrier layer, yet other barrier layers may be used instead or in combination with the aluminium layer. The specific composition of the packaging material is however not directly relevant for the understanding of the present invention, however important it may be for the shelf life of a resulting packaging container filled with content.

In a first processing step I the packaging containers 102 are subjected to a first treatment with vaporized hydrogen peroxide, and following that first treatment the packaging containers 102 are indexed to steps forward to the second processing step II where they are again subjected to a treatment with vaporized hydrogen peroxide. The hydrogen peroxide is provided to the packages via nozzle pipes 114, 120, 122 in this embodiment, two for each processing step. The hydrogen peroxide (or an alternative sterilization agent) may in turn be supplied to the nozzle pipes from a supply via flexible tubes connected to one end of the nozzle pipes.

In the first processing step I the layout is the following: a sterilization unit 104 has a nozzle pipe 114 extending in a vertical direction (coaxial with a longitudinal direction of the packaging container 102). The nozzle pipe is in fluid connection with a source of vaporized hydrogen peroxide, of which there are several alternatives in prior art. When sterilizing the packaging container 102 the nozzle pipe 114, or rather the entire sterilization unit 104 including the nozzle pipe, 114, is lowered so that the nozzle pipe 114 enters the container 102 where it injects the hydrogen peroxide. Following the injection the sterilization unit is retracted upwards to its first position, and has then performed a downward stroke and an upward stroke of identical stroke length. Injection of hydrogen peroxide (or another sterilization agent for that matter) may occur both on the travel downwards and the travel upwards and when the sterilization unit is in its lowermost position, or in any selection of these transitions or positions.

The movement of the sterilization unit may be accomplished e.g. by means of a servomotor synchronized with the indexing of the packages, or by a drive connected to a main drive of the filling machine. The choice of drive is not crucial for the understanding of the present invention.

In the specific embodiment described this first processing step I includes a prefolding and forming step. The packaging container in question may be a so called gable-top package, and the prefolding facilitates adequate folding and sealing in the steps following the sterilization section. For this purpose the sterilization unit 104 is provided with a forming tool 118 which is suspended in rails or rods 116 and which may move independently from the rest of the sterilization unit 104, at least in the directions of the rails 116. Further forming tools (not shown) are present in the first processing step, yet a detailed description of these would obscure the invention in question. The second sterilization unit 106 used in the first processing step is of identical design and a detailed description is therefore considered superfluous.

In processing step III the packages 102, now having a layer of condensed hydrogen peroxide coating all inner surfaces, will be subjected to ultraviolet radiation to enhance the killing of microorganisms. The combination of hydrogen peroxide and ultraviolet radiation is considered to be an established sterilization technique. To protect an operator the radiation treatment is performed in a confined area surrounded by a shield construction as indicated by the dashed frame. The entire process as described herein is performed in a controlled atmosphere such that the sterilization performed is not compromised by reinfection at another stage. In or subsequent to processing step III a stream of hot air may be injected into the containers to remove any residual sterilization agent which otherwise may result in an off taste of a product contained therein.

In order to improve the killing of microorganisms the packages 102 are subjected to a second injection of hydrogen peroxide by means of a sterilisation unit 108 (and 110). This sterilization unit does not include a forming tool, but it does include a shield in the form of a shielding plate 124, effectively forming a roof above the containers 102. The plate or shield 124 has a dual purpose in that it prevents e.g. particles from falling into the container 102 from above, while at the same time confining the injected hydrogen peroxide inside the container 102 after injection. Even further, hydrogen peroxide being injected into a container will be redirected downwards (at least to a higher extent) as it leaves the open end of the container 102, which will ensure sterilization of the upper portion of the container outside, thus preventing reinfection to a higher extent. The relative statement "to a higher extent" refers to a configuration without a shield 124. The plate 124 may preferably cover all packaging containers presently located below the sterilization units 108/110 of the second sterilization step, since this may prevent any debris from falling into a packaging container.

Holes (not visible in the side view of FIGS. 1 and 2) are arranged in the shield 124 for allowing passage of the nozzle pipes 120, 122. In order for the holes to affect the performance and purpose of the shield to as little extent as possible, the holes should be as small as possible. This is turn implies that the diameter of the pipes 120, 122 should be small, and since they still have to deliver a certain amount of sterilization agent the pipe walls will be thin, and the pipes as such will consequently be quite fragile. The holes are preferably circular since the pipes generally have a circular cross section, however both the holes and the pipes may have other shapes. The holes may also have an extension in the axial direction, so as to provide a more efficient gas lock, i.e. to increase the fluid resistance for a fluid wanting to flow in a clearance between an outer perimeter of the pipe and the inner perimeter of the hole.

The second sterilization unit is operationally attached to the first sterilization unit and they move synchronously, in the described embodiments both sterilization units are operationally connected to the same frame 112. More elaborate solutions may be used yet the simplicity of the present solution is preferred. The sterilization unit accelerates rapidly and at an elevated frequency since thousands of packages are treated every hour. For this reason, and in combination with the fragility of the nozzle pipes 120, 122, the nozzle pipe may oscillate slightly during operation. Due to the tight fit between the holes and the outer diameter of the nozzle pipe such oscillations could potentially result in that the nozzle pipe misses the hole ever so slightly. In such a case the sterilization unit will continue to move downwards, and the pipe 120 or 122 will be severely deformed. Another scenario is that the volume below the hole is blocked, e.g. by a faulty packaging container. Such an event may also destroy the nozzle pipe. A direct measure to take would be to increase the diameter of the hole, add guides and/or to reinforce the nozzle pipe in one of many ways.

Figure 2:
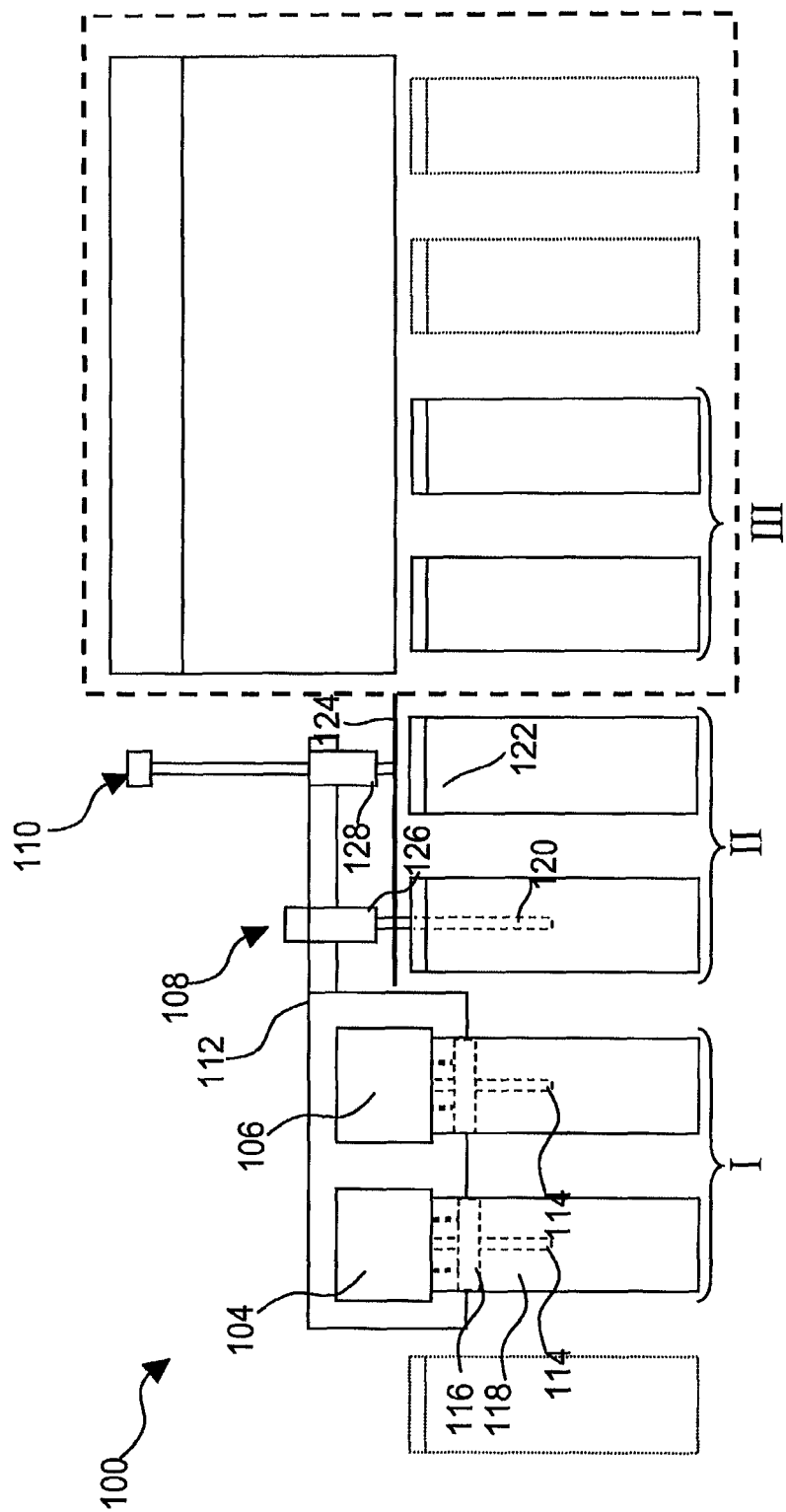
FIG. 2 is a schematical side view of the embodiment of FIG. 1 yet in a second operational state.

According to the present invention each of the nozzle pipes 120 and 122 are positioned by a sleeve 126 and 128 respectively, see FIG. 2. Each sleeve 126, 128 comprises a through opening (not shown) which locates the corresponding pipe 120, 122 firmly, while leaving it movable in an axial direction, i.e. in a longitudinal direction of the nozzle pipe. In the event of the nozzle pipe missing the hole the nozzle pipe 122 will be axially displaced in the sleeve 128, thus preventing irreparable damage of the nozzle pipe. Having said this, it should be emphasized that the displaceable arrangement of the nozzle pipes may be used even if there is no plate 124, since blockages of various types may occur. Also, it may be noted that there obviously are more elaborate ways of arranging the nozzle pipe 120, 122 to be movable or displaceable, such as e.g. a suspension comprising a linkage or a telescopic arrangement, such as a rod and piston arrangement.

In FIG. 2 it is schematically illustrated how the pipe 122 has been displaced in the sleeve 128, while the other pipes and forming tools have engaged a corresponding package. For the purposes of the present invention it is beneficial if the nozzle pipe 122 has a length exceeding the stroke length of the sterilization unit, at least in the simple embodiment where the suspension comprises a sleeve locating the nozzle pipe 122. This will reduce the risk of the pipe nozzle 122 (or 120 for that matter) being forced out of the suspension. In the same and other embodiments it is beneficial if the nozzle pipe has a constant cross section, at least over the stroke length, such that a firm positioning is obtained as the nozzle pipe is displaced in relation to the sterilization unit. Components described in relation to FIG. 1 and hidden inside the container in the view of FIG. 2 are shown in dotted lines in FIG. 2.

In FIG. 2 it is also visualized how the forming tools 118 have performed a relative movement in relation to the rest of the sterilization unit, upwards along the rails 116. In a real installation there are other forming tools performing actions onto the packaging container, which forming tools are not shown in FIG. 2. Movement of the forming tools 118 and the tools not shown may be performed by the same drive as the drive moving the sterilization unit and the relative movement may be realized by a cam or link system. In the case of the forming tools 118 the solution may be even simpler. With the forming tools being movable along the rails 116 and resiliently biased downwards a physical block limiting the downwards movement of the forming tools 118 as the sterilization unit moves downwards may suffice. Even if specific solutions may be inventive the general concept is well known and a skilled person may readily come up with alternative solutions and the construction will not be discussed further within the context of the present invention and embodiments thereof.

Each sterilization unit comprises two pipes or nozzles in the disclosed embodiment. The skilled person realizes that in an embodiment where the packaging containers are indexed a different number of steps, there would also be a different number of nozzles or pipes in each unit, such as one, three, four etc.

Further to this rudimentary embodiment the sterilization unit may comprise a biasing device (not shown), biasing each nozzle pipe downwards, such that the nozzle pipe is automatically repositioned after an accident. A position sensor (not shown) may also be arranged in the filling machine. The position sensor may comprise a photocell device, a contact-breaker device, a pressure sensor or any suitable sensor which may provide an output signal in a situation where a nozzle pipe is displaced. A response to the sensor output may be that the package in question is marked or made possible to track so that it may be easily discarded at a later stage of the processing downstream the sterilization (since the sterilization may be incomplete). Another response may be that the machine operation is halted such that any cause of error may be removed before inducing damage to the sterilization unit or the machine.

The present invention is particularly well adapted for use in sterilization of packaging containers being formed from blanks of packaging material (of the type previously described) formed from a laminate comprising a paper core surrounded by laminated layers of thermoplastic material, and potentially further layers such as an aluminium foil (or other metal foil) for improving the oxygen-barrier properties. The blank is shaped by bending and folding to form a sleeve, the longitudinal edges are joined, and the thus formed sleeve is closed at one end, so as to form a packaging container with an open end. The closing of the one end may be performed by sealing and folding of the sleeve as such, yet it may also be performed by moulding a top of thermoplastic material to the one end of the sleeve. Both these approaches will result in commercially available types of packaging containers, commonly referred to as "carton bottles" and "gable tops", respectively. The first steps in the forming process may be performed before the actual filling machine, such that the packaging container to be is provided to the filling machine as a flattened sleeve, as may be the case for a gable top, or in any intermediate form, such as a flattened rectangular blank, as may be the case for a carton bottle. The packaging material may also be provided to the filling machine in the form of a continuous web of packaging material, which is cut into blanks in a section of the actual filling machine, also an example which may be used for carton bottles. In each of these cases the resulting packaging container will be sterilized and filled from an open end thereof, which end subsequently will be sealed and folded, as oppose to a situation where the package container is sterilized and filled via a spout later to be provided with an opening device.

The invention claimed is:

1. A method of operating a sterilization unit for a filling machine, the sterilization unit comprising a frame movable in an axial direction and first and second nozzle pipes for injecting sterilization agent, the first and second nozzle pipes being movable together with the frame in the axial direction to position each of the first and second nozzle pipes in an interior of a respective one of packaging containers to deliver sterilization agent to the interior of the respective packaging container, the method comprising:
vertically moving the frame downward along the axial direction toward upwardly open ends of the packaging containers, the downward movement of the frame also downwardly moving the first and second nozzle pipes, the first nozzle pipe contacting an obstruction during the downward movement toward the upwardly open ends of the packaging containers so that further downward movement of the first nozzle pipe is stopped;
continuing the downward movement of the frame and the second nozzle pipe when the first nozzle pipe contacts the obstruction and stops the downward movement of the first nozzle pipe, so that the second nozzle pipe passes through the upwardly open end of a corresponding one of the packaging containers and is positioned in the corresponding packaging container; and
injecting sterilization agent from the second nozzle pipe into the corresponding packaging container.

2. A method comprising:
vertically moving a frame downward toward upwardly open ends of packaging containers, the downward movement of the frame also downwardly moving first and second nozzle pipes as well as first and second sleeves, the first nozzle pipe being positioned inside the first sleeve and the second nozzle pipe being positioned inside the second sleeve;
stopping downward movement of the first nozzle pipe as a result of the first nozzle pipe contacting an obstruction during the downward movement toward the upwardly open ends of the packaging containers;
continuing the downward movement of the frame, the first sleeve, the second nozzle pipe and the second sleeve when the first nozzle pipe contacts the obstruction and stops the downward movement of the first nozzle pipe, so that the second nozzle pipe passes through the upwardly open end of a respective one of the packaging containers and is positioned in the respective packaging container; and
injecting sterilization agent from the second nozzle pipe into the respective packaging container.

3. The method of claim 2, wherein at least some of the sterilization agent is injected from the second nozzle pipe into the respective packaging container during downward movement of the second nozzle pipe.

4. The method of claim 2, wherein at least some of the sterilization agent is injected from the second nozzle pipe into the respective packaging container during upward movement of the second nozzle pipe after downward movement of the second nozzle pipe.

5. The method of claim 2, wherein at least some of the sterilization agent is injected from the second nozzle pipe into the respective packaging container during a time between downward movement of the second nozzle pipe and subsequent upward movement of the second nozzle pipe.

6. The method of claim 2, wherein the sterilization agent includes hydrogen peroxide.

7. The method of claim 2, wherein the respective packaging container possesses inner surfaces, and the method further comprises covering all inner surfaces of the packaging container with at least some of the sterilization agent.

8. The method of claim 7, further comprising subjecting the respective packaging container to ultraviolet radiation after injecting the sterilization agent from the second nozzle pipe into the respective packaging container.

9. The method of claim 8, further comprising subjecting the respective packaging container to a stream of heated air after subjecting the respective packaging container to ultraviolet radiation.

10. The method of claim 2, further comprising:
passing the second nozzle pipe through a hole in a shield or plate positioned vertically below the second nozzle pipe, during downward movement of the second nozzle pipe before injecting sterilization agent from the second nozzle pipe into the respective packaging container; and
redirecting at least some of the sterilization agent into the respective packaging container using the shield or plate.

11. A method comprising:
vertically moving a frame downward toward upwardly open ends of first and second packaging containers, the downward movement of the frame also downwardly moving a first nozzle pipe configured to inject sterilization agent in the first packaging container and a second nozzle pipe configured to inject sterilization agent in the second packaging container;
the first nozzle pipe contacting an obstruction during the downward movement toward the upwardly open end of the first packaging container so that further downward movement of the first nozzle pipe is stopped; and
continuing the downward movement of the frame and the second nozzle pipe when the first nozzle pipe contacts the obstruction and stops the downward movement of the first nozzle pipe, so that the second nozzle pipe passes through the upwardly open end of the second packaging container and is positioned in the second packaging container.

12. The method of claim 11, further comprising injecting sterilization agent from the second nozzle pipe into the second packaging container.

13. The method of claim 12, wherein at least some of the sterilization agent is injected from the second nozzle pipe into the second packaging container during downward movement of the second nozzle pipe.

14. The method of claim 12, wherein at least some of the sterilization agent is injected from the second nozzle pipe into the second packaging container during upward movement of the second nozzle pipe after downward movement of the second nozzle pipe.

15. The method of claim 12, wherein at least some of the sterilization agent is injected from the second nozzle pipe into the second packaging container during a time between downward movement of the second nozzle pipe and subsequent upward movement of the second nozzle pipe.

16. The method of claim 12, wherein the sterilization agent includes hydrogen peroxide.

17. The method of claim 12, wherein the second packaging container possesses inner surfaces, and the method further comprises covering all inner surfaces of the second packaging container with at least some of the sterilization agent.

18. The method of claim 17, further comprising subjecting the second packaging container to ultraviolet radiation after injecting the sterilization agent from the second nozzle pipe into the second packaging container.

19. The method of claim 18, further comprising subjecting the second packaging container to a stream of heated air after subjecting the second packaging container to ultraviolet radiation.

20. The method of claim 11, further comprising:
passing the second nozzle pipe through a hole in a shield or plate positioned vertically below the second nozzle pipe, during downward movement of the second nozzle pipe;
injecting sterilization agent from the second nozzle pipe into the respective second packaging container; and
redirecting at least some of the sterilization agent into the respective second packaging container using the shield or plate.

21. The method of claim 11, wherein the vertically moving of the frame downward occurs during a first downward movement stroke of the frame, and the packaging containers are a first set of packaging containers, the method further comprising vertically moving the frame downward along the axial direction toward upwardly open ends of a second set of packaging containers during a second downward movement stroke of the frame to position the first nozzle pipe in one of the packaging containers of the second set of packaging containers without contacting an obstruction and to position the second nozzle pipe in another one of the packaging containers of the second set of packaging containers without contacting an obstruction.

* * * * *